United States Patent [19]

Shoesmith, deceased

[11] Patent Number: Plant 6,222

[45] Date of Patent: Jul. 12, 1988

[54] CHRYSANTHEMUM PLANT NAMED DAPPER

[75] Inventor: Leonard H. Shoesmith, deceased, late of Westfield, England, by May Victoria Shoesmith, executrix

[73] Assignee: Ball PanAm Plant Company, Parrish, Fla.

[21] Appl. No.: 891,315

[22] Filed: Jul. 31, 1986

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Dapper having flat capitulum form and single capitulum type; ray florets which are clear white in color and frequently are tube-shaped at the base, flaring widely for remainder of floret; eight week flowering response, and ability to be grown in nine cm pots year around in most areas.

1 Drawing Sheet

The present invention comprises a new and distinct cultivar of *Chrysanthemum morifolium,* Ramat., hereinafter referred to by the cultivar name Dapper.

Dapper is a product of a planned breeding program which had the objective of creating new Chrysanthemum cultivars with unique colors and flower forms suitable for 4" pots in year around programs.

Dapper was originated from a hybridization made in a controlled breeding program in Westfield-Woking, England in 1979. The male and female parents are unknown at this time.

Dapper was discovered and selected as one flowering plant within the progeny of the cross by Leonard H. Shoesmith in November of 1980 in a controlled environment in West Chicago, Ill.

The first act of asexual reproduction of Dapper was accomplished when vegetative cuttings were taken from the initial selection in February of 1981 in a controlled environment in West Chicago, Ill. by a technician working under formulations established and supervised by Leonard H. Shoesmith. Horticultural examination of selected units initiated in June of 1981 has demonstrated that the combination of characteristics as herein disclosed for Dapper are firmly fixed and are retained through successive generations of asexual reproduction.

Dapper has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Dapper, which in combination distinguish this Chrysanthemum as a new and distinct cultivar:

1. Flat capitulum form.
2. Single capitulum type, up to 60 mm across.
3. Clear white ray florets, many of which are tube shaped at base, flaring widely for remainder of petal. Tube length varies from 1 mm to 14 mm long.
4. Ray florets up to 25 mm long.
5. Disc florets deep yellow when mature, light yellow-green when immature.

6. Eight week flowering response.
7. Ability to grow in 9 cm pots year around in most areas, requiring little B-9.

Of the many commercial cultivars known to the present inventor, the most similar in comparison to Dapper is White Stardom. In comparison to White Stardom, Dapper is one week later in flowering, and is not suitable as a garden variety in many areas where White Stardom is. The flower type, color and habit of Dapper are similar to those same characteristics of White Stardom.

The accompanying photographic drawing shows typical inflorescence and foliage characteristics of Dapper, with colors being as nearly true as possible with illustrations of this type. The drawing sheet comprises a black and white photograph which consequently depicts the clear white ray floret color of Dapper. The disc florets have been colored to precisely show disc floret color.

In the following description, color references are made to The Royal Horticultural Colour Chart. The color values were determined at approximately 8:30 a.m. on July 7, 1986 under 4000 foot candles of light intensity at Parrish, Fla.

Classification:

*Botanical.*—*Chrysanthemum morifolium,* Ramat., cv Dapper.

*Commercial.*—4" daisy pot mum.

INFLORESCENCE

A. Capitulum:

*Form.*—Flat.

*Type.*—Single.

*Diameter across face.*—60 mm.

B. Corolla of ray florets:

*Color (general tonality from a distance of three meters).*—White.

*Ray floret color (both upper and under surfaces-)*—155B.

*Tube color.*—155B.

C. Corolla of disc florets:

*Color (mature).*—Yellow.

*Color (immature).*—Yellow-green.

D. Reproductive organs:

*Androecium.*—Present in disc florets only; many.

*Gynoecium.*—Present in ray and disc florets; many.

PLANT

A. General appearance:

*Height.*—15–20 cm above edge of pot when grown well.

B. Foliage:

*Color* (*upper surface*).—147A.

*Color* (*under surface*).—147B.

*Shape.*—Deeply lobed and slightly serrate-ovate.

I claim:

1. A new and distinct cultivar of Chrysanthemum named Dapper, as described and illustrated, and particularly characterized as to uniqueness by its flat capitulum form and single capitulum type; ray florets which are clear white in color and frequently are tube-shaped at the base, flaring widely for remainder of floret; eight week flowering response, and by its ability to be grown in nine cm pots year around in most areas.

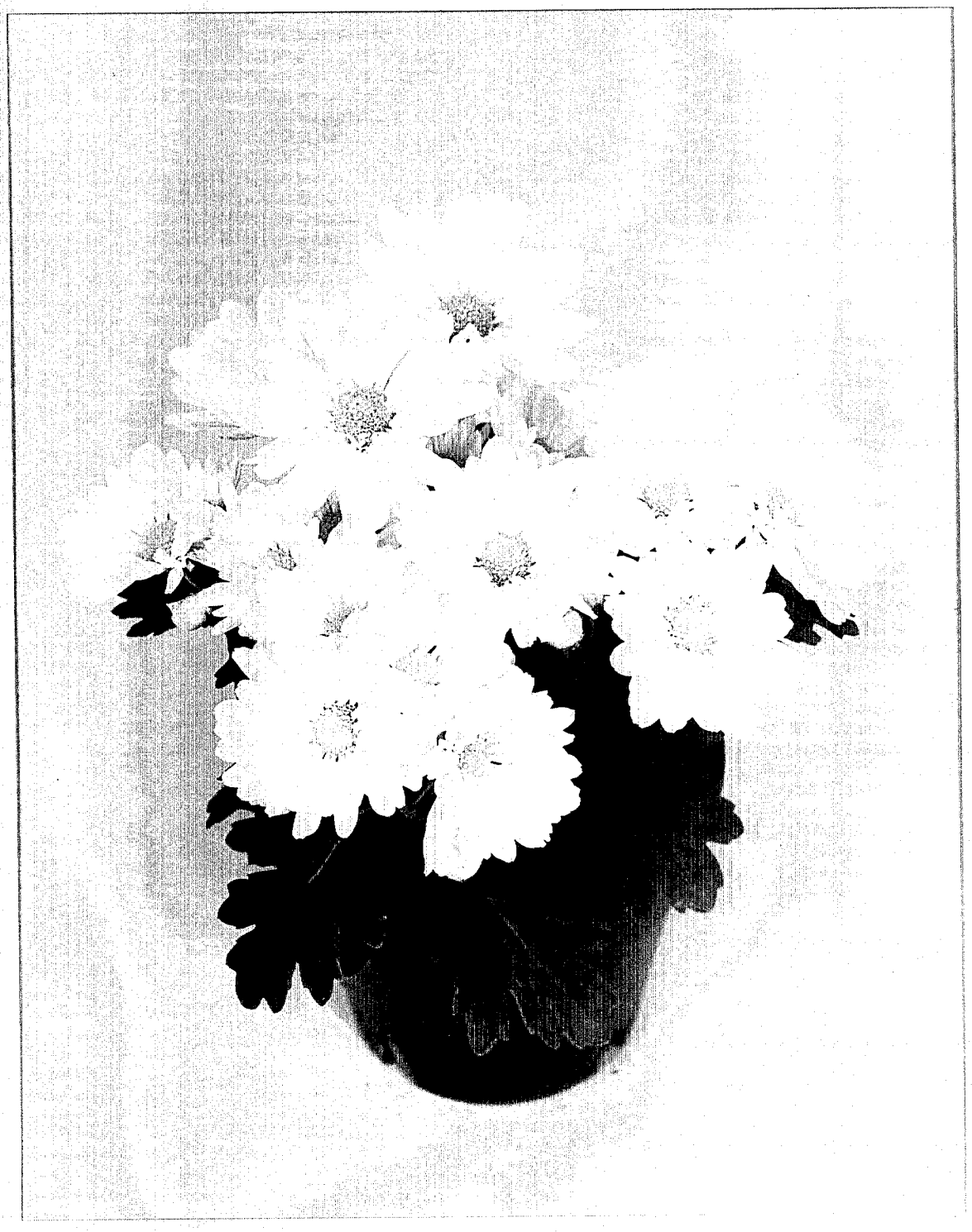

* * * * *